(12) United States Patent
Haley et al.

(10) Patent No.: US 9,888,837 B2
(45) Date of Patent: Feb. 13, 2018

(54) FIBER OPTIC ILLUMINATION DEVICE AND METHOD OF MANUFACTURING

(75) Inventors: Patrick Haley, Elk River, MN (US); Ronald Zimmermann, Hudson, WI (US); Mark Peterson, Chanhassen, MN (US)

(73) Assignee: I-Tek Medical Solutions, Inc., White Bear Lake, MN (US)

( * ) Notice: Subject to any disclaimer, the term of this patent is extended or adjusted under 35 U.S.C. 154(b) by 622 days.

(21) Appl. No.: 13/373,720

(22) Filed: Nov. 28, 2011

(65) Prior Publication Data
US 2013/0137935 A1 May 30, 2013

(51) Int. Cl.
| | |
|---|---|
| *A61B 1/07* | (2006.01) |
| *G02B 6/32* | (2006.01) |
| *G02B 6/26* | (2006.01) |
| *A61B 1/00* | (2006.01) |

(52) U.S. Cl.
CPC .............. *A61B 1/07* (2013.01); *A61B 1/0011* (2013.01); *A61B 1/0017* (2013.01); *G02B 6/262* (2013.01); *G02B 6/32* (2013.01); *Y10T 29/49908* (2015.01)

(58) Field of Classification Search
CPC .... A61B 2018/2266; A61B 2018/2288; A61B 2018/2255
See application file for complete search history.

(56) References Cited

U.S. PATENT DOCUMENTS

| | | | |
|---|---|---|---|
| 3,941,121 A | 3/1976 | Ollinger et al. | |
| 4,135,781 A * | 1/1979 | Archer ................. | G02B 6/3835 156/196 |
| 4,191,447 A * | 3/1980 | Borsuk ................ | G02B 6/2552 29/522.1 |
| 4,398,790 A * | 8/1983 | Righini .................. | A61B 18/22 385/33 |
| 4,562,832 A | 1/1986 | Wilder et al. | |
| 4,870,952 A * | 10/1989 | Martinez ....................... | 362/572 |
| 5,005,108 A | 4/1991 | Pristash et al. | |
| 5,275,593 A * | 1/1994 | Easley .................... | A61F 9/008 604/27 |
| 5,351,168 A * | 9/1994 | Easley .......................... | 362/572 |
| 5,434,940 A * | 7/1995 | Roff et al. ..................... | 385/91 |
| 5,520,611 A | 5/1996 | Rao et al. | |

(Continued)

FOREIGN PATENT DOCUMENTS

JP     2834811 B2 * 12/1998 ........... G02B 6/2552

OTHER PUBLICATIONS

ProQuest Machine Translation of JP 2834811 B2, Dec. 1998.*

(Continued)

*Primary Examiner* — Michelle R Connelly
(74) *Attorney, Agent, or Firm* — Holzer Patel Drennan

(57) ABSTRACT

A fiber optic illumination device suitable for use in medical procedures and other application requiring the delivery of light to limited access locations is disclosed. The illumination device defines a proximal terminal structure derived from the optical fiber having a greater surface area than the diameter of the optical fiber and a distal terminal structure derived from the optical fiber having a greater surface area than diameter of the optical fiber. An integral light communication path is defined between the proximal terminal structure and the distal terminal structure. A method of manufacturing the fiber optic illumination device is also disclosed.

11 Claims, 6 Drawing Sheets

(56) References Cited

U.S. PATENT DOCUMENTS

| | | | |
|---|---|---|---|
| 5,545,153 A * | 8/1996 | Grinblat | A61F 9/007 604/117 |
| 5,598,497 A | 1/1997 | Roller | |
| 5,613,751 A | 3/1997 | Parker et al. | |
| 5,618,096 A | 4/1997 | Parker et al. | |
| 5,770,132 A * | 6/1998 | Yamamura | G02B 6/3855 156/294 |
| 6,004,263 A | 12/1999 | Nakaichi et al. | 600/176 |
| 6,874,925 B2 | 4/2005 | Page et al. | |
| 7,090,411 B2 | 8/2006 | Brown | |
| 7,470,269 B2 * | 12/2008 | Auld | A61B 90/36 606/15 |
| 7,677,812 B2 * | 3/2010 | Castagna | H01R 13/562 385/69 |
| 2002/0028047 A1 * | 3/2002 | Yasuda | G02B 6/2552 385/79 |
| 2002/0076157 A1 * | 6/2002 | Kropp | 385/38 |
| 2003/0035620 A1 | 2/2003 | Manolatu | 385/33 |
| 2003/0174956 A1 | 9/2003 | Viens | 385/43 |
| 2004/0242971 A1 | 12/2004 | Holland et al. | |
| 2005/0105877 A1 * | 5/2005 | Nappi et al. | 385/140 |
| 2005/0207706 A1 | 9/2005 | Schmidt et al. | 385/55 |
| 2008/0031573 A1 | 2/2008 | Droege et al. | 385/78 |
| 2008/0037933 A1 * | 2/2008 | Furman et al. | 385/31 |
| 2010/0316344 A1 | 12/2010 | Bylander et al. | 385/134 |
| 2011/0252634 A1 * | 10/2011 | Pons | G02B 6/3887 29/729 |

OTHER PUBLICATIONS

Young, Lee W., International Search Report and Written Opinion of the the International Searching Authority, dated Feb. 5, 2013, pp. 4, 7-10.

PCT International Preliminary Report of Patentability and Written Opinion, dated Jun. 12, 2014.

* cited by examiner

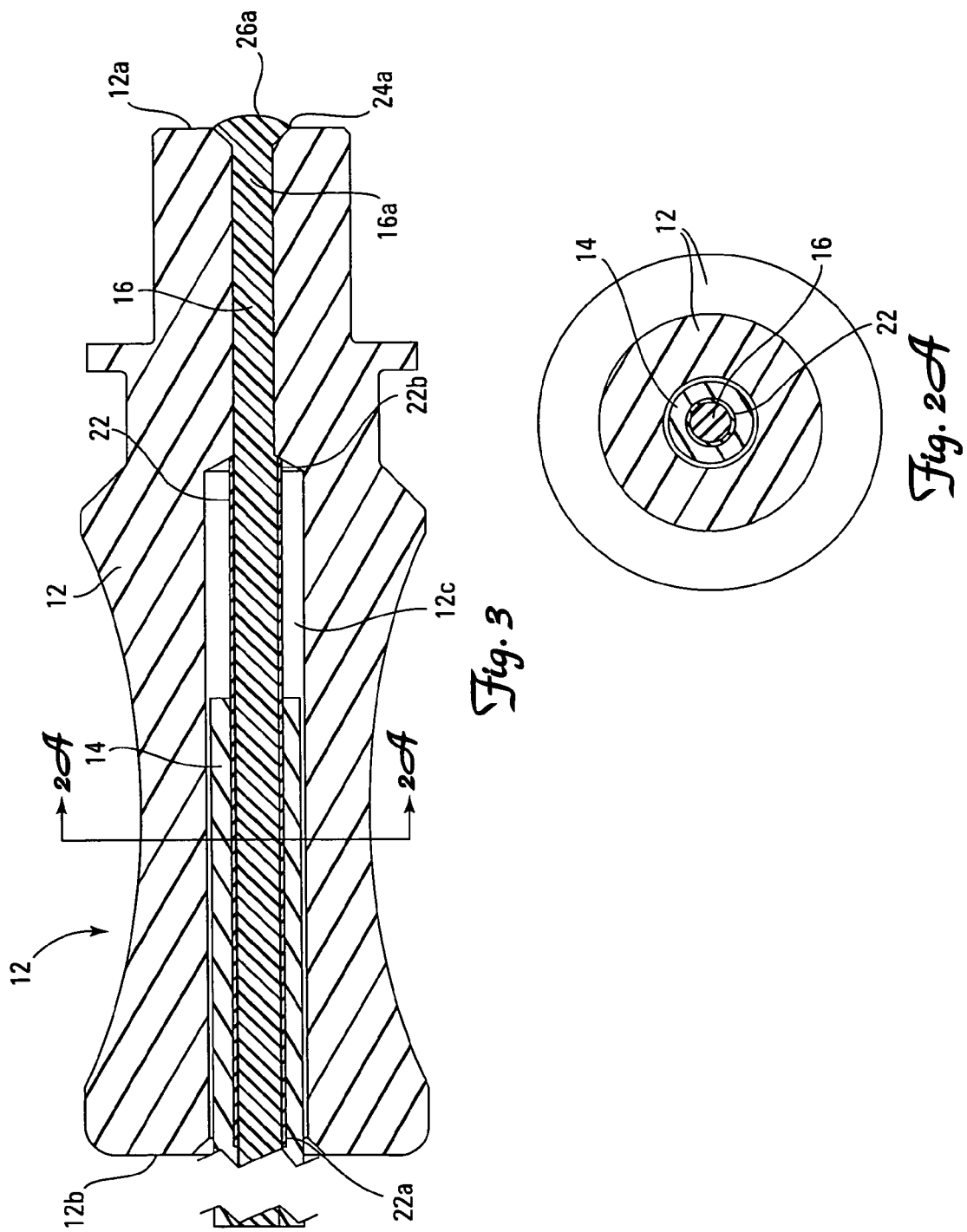

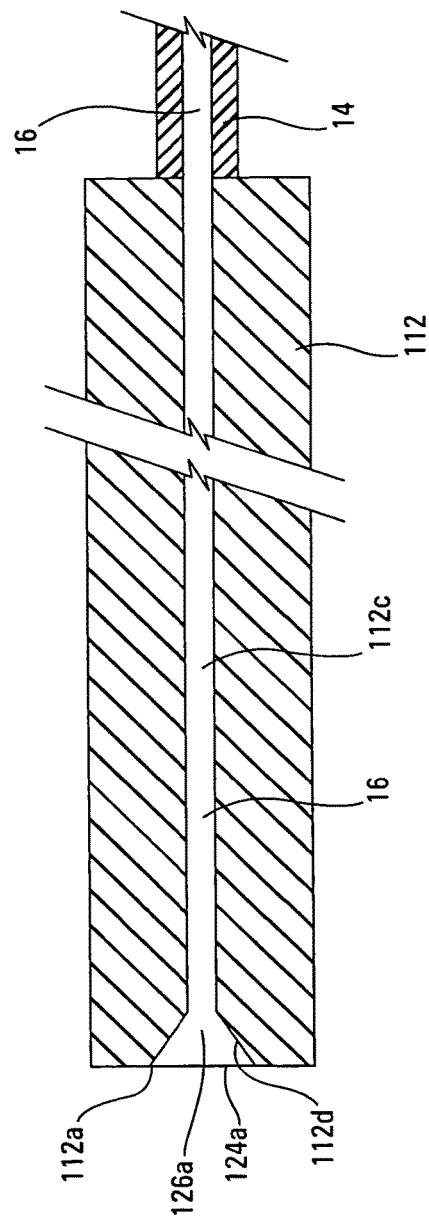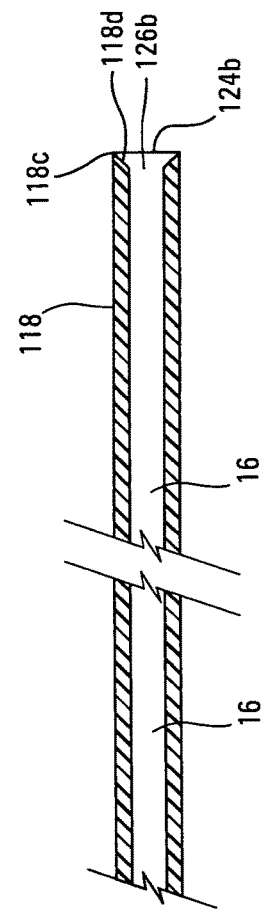
Fig. 4A
Fig. 4B

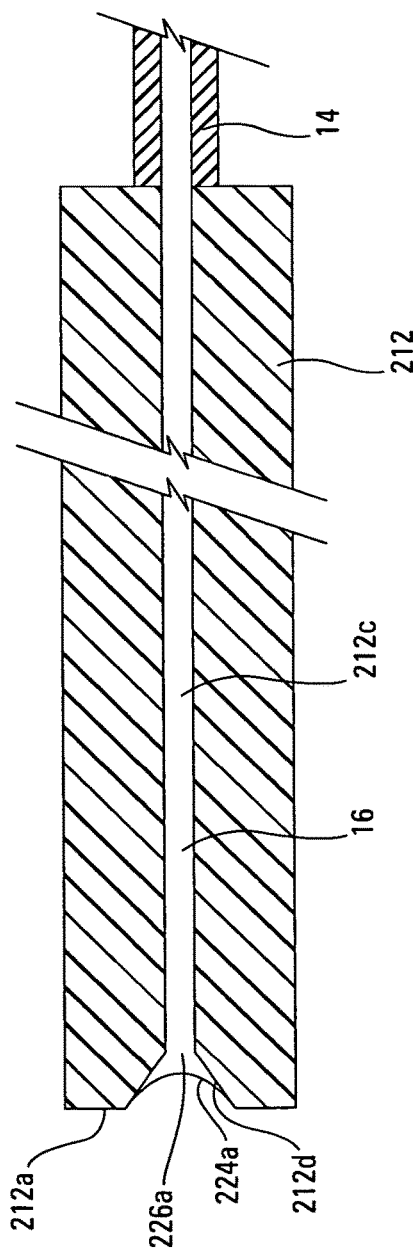
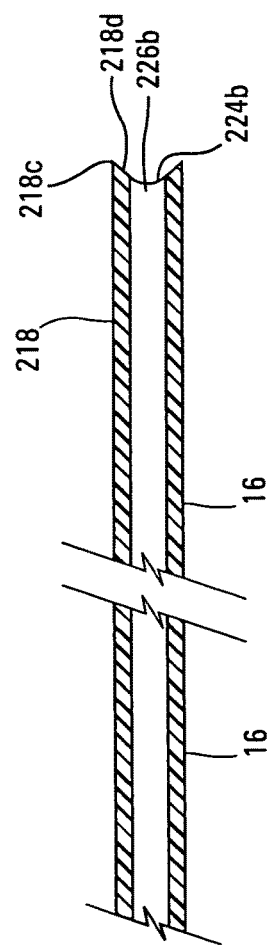
Fig. 5A
Fig. 5B

FIBER OPTIC ILLUMINATION DEVICE AND METHOD OF MANUFACTURING

FIELD OF THE INVENTION

The invention relates to an improved fiber optic illumination device that attaches to a light source and is used to precisely deliver an increased efficiency of total light transmission to limited accessibility surgical sites. The invention can also be used for other medical and non-medical application requiring illumination of limited access areas.

BACKGROUND

The use of optical fibers or groups of optical fibers attached to different types of light sources to illuminate areas having limited accessibility and lacking a clear line of sight with an external light source is well known in the art. Use in medical applications is sometimes limited by the buildup of excess temperature at the distal or light emitting end of the optical fiber. This is particularly limiting in the case of plastic optical fibers. This is at least partly due to the inherent inefficiency of typical optical fibers to deliver light at specific target areas and the increased emission of light from the attached light source required to provide adequate illumination to a surgical site.

At the proximal end of the optical fiber, current fiber optic illumination systems require an optical fiber with a relatively large diameter and/or a relatively large Numerical Aperture to collect an adequate amount of the typically highly divergent light from an attached light source.

Further, at the distal end, current fiber optic illumination systems suffer from excess light scattered outside the target area due to an inability to emit the high order mode light collected at the proximal end and distribute it at the distal end as low order mode light. Existing fiber optic illumination systems require a relatively large diameter fiber to deliver similar light intensities on a relatively small target area.

What is clearly needed, therefore, is a fiber optic illumination system allowing a relatively small diameter optical fiber to collect high order mode light at the proximal end, transmit the light along the length of the optical fiber, and distribute lower order mode light at the distal end.

SUMMARY

In one embodiment, the invention is directed to an illumination device having an optical fiber defining a proximal end, a distal end, a length, a core fiber layer and a cladding layer surrounding at least part of the core fiber layer. A connector is attached to the proximal end of the optical fiber and defines a proximal end and a distal end, with the optical fiber extending into the connector. At the distal end of the optical fiber is a distal tube into which the optical fiber extends. The proximal end of the optical fiber is configured into a proximal terminal structure derived from the optical fiber, which causes high order mode light entering the illumination device to be converted to low order mode light and the distal end of the optical fiber is configured into a distal terminal structure derived from the optical fiber, which causes high order mode light to be converted into low order mode light emitted from the illumination device. The proximal distal structure, distal terminal structure and at least the fiber core are integral with each other.

In another embodiment, the invention is directed to an illumination device having an optical fiber defining a proximal end, a distal end, a length, a diameter, a core fiber layer and a cladding layer surrounding at least part of the core fiber layer. A connector is attached to the proximal end of the optical fiber and defines a proximal end, a distal end, and a channel extending into the connector, with the channel defining a diameter. A crimp sleeve surrounds a portion of the optical fiber and is secured over the outer dimension of the optical fiber by crimping the crimp sleeve. Surrounding a portion of the crimp sleeve is a proximal strain relief member, with the proximal strain relief member being secured to the outer diameter of the channel extending through the connector. A distal tube is attached to the distal end of the optical fiber and defines a distal end and is configured to receive the optical fiber. The proximal end of the optical fiber is configured into a proximal terminal structure derived from the optical fiber having a greater surface area than the diameter of the optical fiber which causes high order mode light entering the illumination device to be converted to low order mode light and the distal end of the optical fiber is configured into a distal terminal structure having a greater surface area than the diameter of the optical fiber and causes high order mode light to be converted into low order mode light which is emitted from the illumination device. The proximal terminal structure, distal terminal structure and core fiber are integral with each other.

In an alternative embodiment, the invention is directed to a method of manufacturing a fiber optic illumination device, including the steps of:

a. preparing a proximal section of the illumination device by:
  i. providing an optical fiber defining a proximal end, a distal end, an outer diameter, a length, a cladding layer and a core layer;
  ii. trimming the proximal end and the distal end of the optical fiber;
  iii. sliding a length of crimp sleeve over the proximal end of the optical fiber, allowing a length of optical fiber to extend from the proximal end of the crimp sleeve;
  iv. crimping the crimp sleeve with sufficient mechanical force to cause the crimp sleeve to take a permanent set to secure the crimp sleeve to the optical fiber without damaging the optical fiber;
  v. providing a connector defining a proximal end, a distal end and a channel extending there through;
  vi. inserting and attaching a proximal strain relief member into the distal end of the channel in a manner allowing a portion of the proximal strain relief member to extend distally from the connector;
  vii. fitting the optical fiber with attached crimp sleeve into the connector through the proximal strain relief member to allow a length of optical fiber to extend from the proximal end of the connector;
  viii. exposing the end of the optical fiber extending from the proximal end of the connector to a sufficient amount of air and heat to cause the proximal end of the optical fiber to reflow, creating a first structure extending from the proximal end of the connector having a diameter wider than the optical fiber prior to reflowing; and b. preparing a distal end of the illumination device by:
  i. providing a distal tube;
  ii. sliding the distal tube over the optical fiber allowing a length of optical fiber to extend from the distal end of the distal tube;
  iii. crimping the distal tube with sufficient mechanical force to cause the crimp sleeve to take a permanent set to secure the crimp sleeve to the optical fiber without damaging the optical fiber; and iv. exposing the end of the optical fiber extending from the distal end of the distal tube with a sufficient amount of air and heat to cause the proximal end of the optical fiber to reflow, creating a second structure extending from the distal end of the connector having a diameter wider than the optical fiber prior to reflowing, resulting in a fiber optic illumination device with an integral light communication path between the proximal end of the illumination device and the distal end of the illumination device.

BRIEF DESCRIPTION OF THE DRAWINGS

FIG. 2a is a lateral cross section taken through lines 2a-2a of FIG. 1.

FIG. 3 is a longitudinal cross section taken through the connector.

FIG. 4a is a longitudinal cross section taken through the proximal section of an alternative embodiment of the invention.

FIG. 4b is a longitudinal cross section taken through the distal section of an alternative embodiment of the invention.

FIG. 5a is a longitudinal cross section taken through the proximal section of another embodiment of the invention.

FIG. 5b is a longitudinal cross section taken through the distal section of another embodiment of the invention.

DETAILED DESCRIPTION

Figure 1:
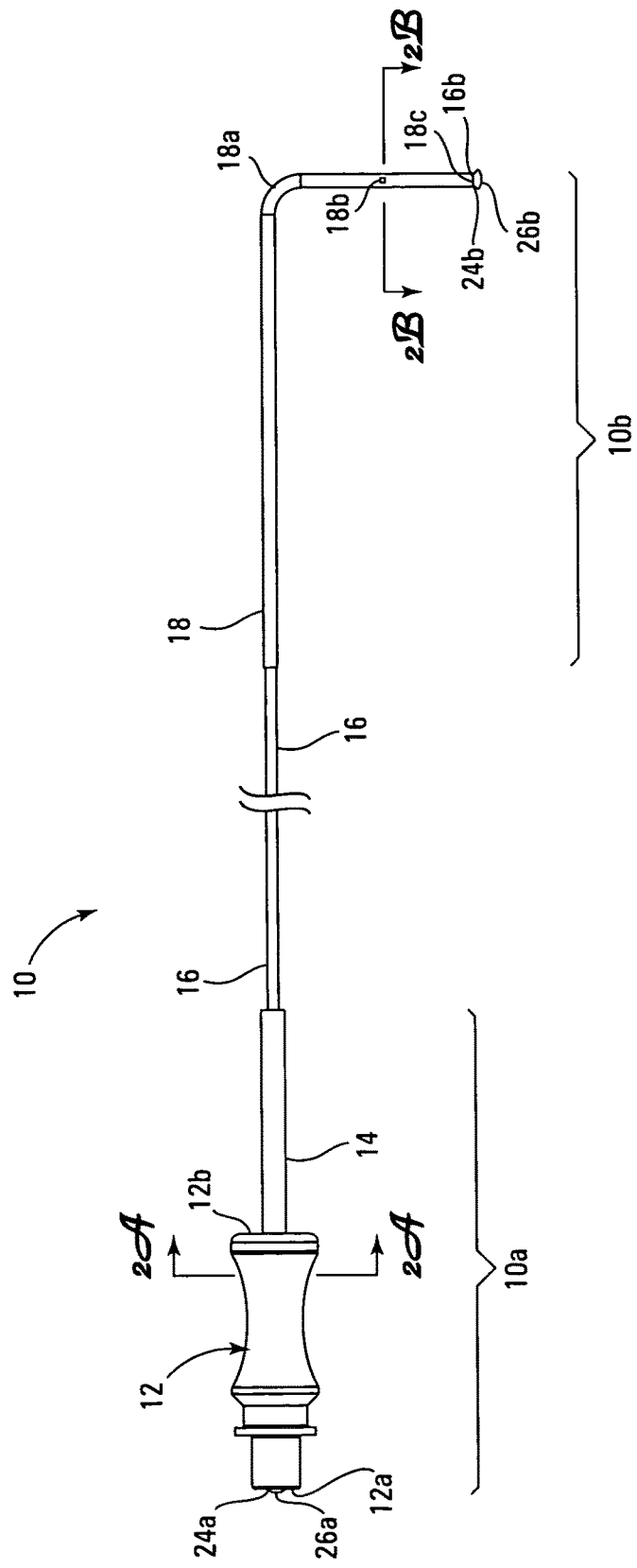
FIG. 1 is a plan view of the fiber optic illumination device of the invention.

The particulars shown herein are by way of example and for purposes of illustrative discussion of the invention only and are presented in the cause of providing what is believed to be the most useful and readily understood description of the principles and conceptual aspects of the invention. The drawings are in simplified form and are not to precise scale. In this regard, no attempt is made to show structural details of the invention in more detail than is necessary for the fundamental understanding of the invention, the description taken with the drawings making apparent to those skilled in the art how the several forms of the invention may be embodied in practice. Wherever possible, same or similar reference numerals are used in the drawings to refer to the same or like parts or steps.

NOMENCLATURE

10 Fiber Optic Illumination Device
10a Proximal Section of Fiber Optic Illumination Device
10b Distal Section of Fiber Optic Illumination Device
12 Connector
12a Proximal End of Connector
12b Distal End of Connector
12c Connector Channel
14 Proximal Strain Relief Member
16 Optical Fiber
16a Proximal End of Optical Fiber
16b Distal End of Optical Fiber
18 Distal Tube
18a Bend in Distal Tube
18b Crimp
18c Distal End of Distal Tube
20 Cladding
22 Crimp Sleeve
22a Proximal End of Crimp Sleeve
22b Distal End of Crimp Sleeve
24 Optical Fiber Core
24a Proximal End of Optical Fiber Core
24b Distal End of Optical Fiber Core
26a Proximal Terminal Structure
26b Distal Terminal Structure
50 Providing Optical Fiber
52 Trim Proximal End and Distal End of Optical Fiber
54 Slide Crimp Sleeve Over Distal End of Optical Fiber with Length of Optical Fiber Proximally Extending
56 Crimping Crimp Sleeve to Optical Fiber
58 Provide Connector
60 Insert and Attach Proximal Strain Relief Member to Connector
62 Fit Optical Fiber/Crimp Sleeve through Proximal Strain Relief Member and Connector so
64 Expose Proximally Extending Optical Fiber to Sufficient Heat to Reflow Length of Optical Fiber Proximally Extending from Connector
66 Provide Distal Tube
68 Slide Distal Tube over Optical Fiber Allowing Length of Optical Fiber to Distally Extend
70 Crimp Distal Tube to Secure to Optical Fiber
72 Expose Distally Extending Optical Fiber to Sufficient Heat to Reflow Length of Optical Fiber Distally Extending from Distal Tube
112 Connector
112a Proximal End of Connector
112b Distal End of Connector
112c Connector Channel
112d Concavity
118 Distal Tube
118c Distal End of Distal Tube
118d Concavity
124b Distal End of Optical Fiber Core
126a Proximal Terminal Structure
126b Distal Terminal Structure
212 Concavity
212a Proximal End of Channel
212c Channel
212d Concavity
218 Distal Tube
218c Distal End of Distal Tube
218d Concavity
224b Distal End of Optical Fiber Core
226a Proximal Terminal Structure
226b Distal Terminal Structure Definitions "Distal" means further from the point controlled by the operator (e.g., physician or technician) of a device.

"Glass Optical Fiber" means an optical fiber that is comprised one or more hard, amorphous or crystalline materials. This is generally not pure "glass" in the technical sense but rather one or more multiple varieties of fused silica, doped silica, doped fused silica or other materials such as sapphire and similar materials. Glass Optical Fiber may also refer to optical fibers having a "glass" core (with respect to the description above and polymer cladding layer(s).

"High Order Mode Light" means light that enters an optical fiber at a relatively high transverse path to the longitudinal axis of the optical fiber. High order mode light can be so transverse as to be greater than the critical angle and therefore penetrate the interface between the core and cladding and be permanently lost through the cladding.

"Lateral Cross Section" means a cross section taken through a substantially perpendicular angle to the length of an object.

"Longitudinal Cross Section" means a cross section taken through a substantially parallel angle to the length of an object.

"Low Order Mode Light" means light that enters an optical fiber at an angle either parallel to or relatively modestly transverse to the longitudinal axis of the optical fiber.

"Numerical Aperture" (NA) means The light-gathering ability of an optical fiber, as determined by the square root of the difference of the squares of the refractive indexes of the core ($n_1$) and the cladding ($n_2$), and as expressed in the equation:

$$NA=SQRT(n_1^2-n_2^2).$$

Fiber optic transmission systems (FOTS) are based on the principle of total internal reflection, meaning that all light injected into the fiber is retained in the fiber. The objective is to retain all components of the optical signal in the core. However, a light source naturally injects some light rays into the core at angles greater than the critical angle, which is measured relative to the parallel with the longitudinal axis of the optical fiber core. At such severe angles, the incident light rays penetrate the core/clad interface and enter the cladding, where they will be lost. The numerical aperture essentially is an indication of how wide an angle of incident light will be captured and propagated by the optical fiber. For example, an optical fiber with a small NA requires more directional, focused, light, whereas a fiber with a large NA does not. The higher NA allows the fiber to accept more light at a greater angle relative to the fiber's longitudinal axis and thus propagate higher modes.

"Plastic Optical Fiber" means an optical fiber made out of polymeric materials, with the core often being a polymer such as an acrylate material and the cladding being a polymer with a lower refractive index such as fluorinated polymers.

"Proximal" means closer to the point controlled by the operator (e.g., physician or technician) of a device.

"Reflow" means applying sufficient pressure and/or temperature to a polymeric or glass or crystalline material to cause it to change configuration.

"SCFM" means standard cubic feet per minute. SCFM is the volumetric flow of a gas corrected to "standardized" conditions of temperature and pressure. It is understood that there is no universally accepted set of standardized conditions.

"Terminal Structure" as used herein means a structure integral with at least the fiber core configured to have a greater surface area than the diameter of the fiber core.

"Tg" means glass transition in glass forming materials characterized by a change in phase from solid to liquid upon the application of heat.

Construction

FIG. 1 shows a plan view of the fiber optic illumination device 10 of the present invention. It is seen that a connector 12 is attached proximate to the proximal end 24a of an optical fiber 16 and defines a proximal end 12a and a distal end 12b and a channel 12c extending the length of the connector 12. The connector 12 is of conventional design and is used to attach the fiber optic illumination device 10 to an external light source (not shown). The optical fiber 16 extends through and from a proximal strain relief member 14, which is attached to and extends distally from the distal end 12b of the connector 12 and provides support and protection for the optical fiber 16 during use. Both plastic optical fiber material and glass optical fiber material are suitable to be used when practicing the present invention. Proximal strain relief member 14 can be made of any suitable thermoplastic tubing such as Tygon®, nylon, PTFE, silicone, polyurethane, braided tubing or any other material possessing suitable physical and biocompatible properties and serves to generally support, protect and more specifically prevent the optical fiber 16 from kinking during use. The connector 12 and proximal strain relief member 14 are attached to each other by any of several chemical and/or mechanical means including but not limited to interference fitting, gluing, crimping and thermal attachment. In one embodiment, the outer diameter of the proximal strain relief member 14 is greater than the inner diameter of the channel 12c extending longitudinally through the channel 12c of connector 12 resulting in an interference fit attachment.

In one embodiment, optical fiber 16 and connector 12 are fitted together using a crimp sleeve 22 which is crimped over the outer surface (cladding 20) of the optical fiber 16. In one embodiment the crimp sleeve 22 is made of stainless steel hypotube and in another embodiment aluminum hypotube, however, the crimp sleeve 22 can also be made of additional materials possessing adequate strength and mechanical characteristics. The optical fiber 16 with attached crimp sleeve 22 is inserted into the channel 12c which extends longitudinally through the connector 12 which, as described above has had previously attached a proximal strain relief member 14. The optical fiber 16 is attached to the connector 12 by means of treating the extending proximal end 16a of the optical fiber 16 with a sufficient amount of heat and air to cause the distal end 16a to reflow. In one embodiment, air having an approximate temperature between 400 degrees F. and 500 degrees F. at an airflow of approximately 5-20 standard cubic feet per minute for a period of approximately 2-5 seconds reaches the Tg of the base material causing the proximal end 16a of the optical fiber 16 to reach a reflow state, resulting in the simultaneous melting of the core 24a and cladding 20 and the formation of a proximal terminal structure 26a integral with the core 24. The formation of the proximal terminal structure 26a serves to secure the optical fiber 16 to the connector 12 without the use of chemical or mechanical fasteners and also provides a structure similar to a lens, which is integral with at least the core 24 along the length of the fiber optic illumination device 10. It is noted that due to the extra dimension inherent in the convex proximal terminal structure 26a, a greater surface area is exposed than the diameter of the optical fiber 16 would have if squarely trimmed.

Toward the distal end 16b of the optical fiber 16 is a distal tube 18 through which the optical fiber 16 passes and which serves to provide shape, strength and stability to the fiber optic illumination device 10 during use when it is normally securely attached to a surgical retractor or other surgical hardware during a procedure. In one embodiment the distal tube 18 is made of stainless steel and in another embodiment, aluminum, however, the distal tube 18 can also be made of additional materials possessing adequate strength and formability. It is noted that in one embodiment, the distal tube 18 is crimped 18b to the cladding 20 defining the outer surface of the optical fiber 16. In one embodiment, the optical fiber 16 is attached to the distal end 18c of the distal tube 18 by means of treating the optical fiber 16 with a sufficient amount of heat and air to cause the distal end 16b of the optical fiber 16 to reflow. Air having an approximate temperature between 400 degrees F. and 500 degrees F. at an airflow of approximately 5-20 standard cubic feet per minute for a period of approximately 2-5 seconds reaches the Tg of the base material causing the distal end 16b of the optical fiber 16 to approach the reflow state, resulting in the simultaneous expansion of the core 24 and cladding 20 and the formation of a distal terminal structure 26b. The formation of the distal terminal structure 26b serves to secure the optical fiber 16 within the distal tube 18 without the use of chemical or mechanical fasteners and also provides a structure similar to a lens, but which is integral with at least the core 24 along the length of the fiber optic illumination device 10 between the proximal terminal structure 26a and the distal terminal structure 26b, allowing uninterrupted light communication between the proximal terminal structure 26a and distal terminal structure 26b. It is noted that due to the extra dimension inherent in the convex distal terminal structure 26b, a greater surface area is exposed than the diameter of the optical fiber 16 would have if squarely trimmed. It is understood that the distal tube 18 shown in FIG. 1 can be pre-formed into any shape required by the particular retractor or surgical hardware used as well as the preferences of the surgeon performing the procedure and should therefore not be considered as being limited to the particular shape shown. It is also understood that the distal tube 18 could be made of a malleable material able to be quickly shaped into any shape desired.

FIG. 2a is a lateral cross section taken through the lines 2a-2a of FIG. 1. It is seen that the optical fiber 16 is surrounded at least part of the length (unnumbered) of the connector 12 by the crimp sleeve 22 which in turn is surrounded by the proximal strain relief member 14 which is attached to and extends from the distal end 12b of the connector 12.

Figure 2B:
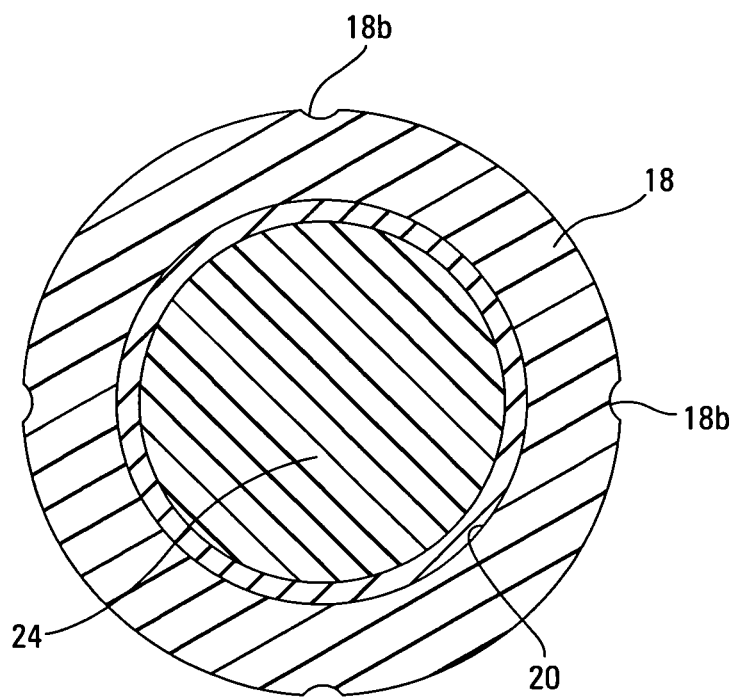
FIG. 2b is a lateral cross section taken through lines 2b-2b of FIG. 1.

FIG. 2b is a lateral cross section taken through the lines 2b-2b of FIG. 1. It is seen that the core 24 is surrounded by the cladding 20, which is surrounded by the distal tube 18. A crimp 18b is impressed into the distal tube 18 which serves to stabilize and secure the optical fiber 16 within the illumination device 10. While a certain number of crimps 18b are impressed into the distal tube 18 it is understood that this is for purposes of illustration only and that lesser or greater numbers of crimps 18b as well as different configurations (i.e., at different positions on the distal tube 18) are within the scope of the invention.

FIG. 3 is a longitudinal cross section taken through the connector 12. It is seen that at least the core 24 extends the length (unnumbered) of the connector 12, allowing an integral light path along the length of the fiber optic illumination device 10 of the present invention.

FIG. 4a shows an alternative embodiment of the proximal terminal structure 126a wherein the optical fiber 16 fits in a beveled concavity 112d at the proximal end 112a of the channel 112c. It is noted that the exposed end (unnumbered) of the proximal terminal structure is flush with the proximal end 112a of the connector 112 and thus presents a greater surface area than the diameter of the optical fiber 16 would have if squarely trimmed.

FIG. 4b similarly shows an alternative embodiment of the distal terminal structure 126b wherein the optical fiber 16 ends at a beveled concavity 118d at the distal end 118c of the distal tube 118. It is noted that the exposed end (unnumbered) of the distal terminal structure 126b is flush with the distal end 118c of the distal tube 118 and thus presents a greater surface area than the diameter of the optical fiber 16 would have if squarely trimmed. While the distal terminal structure 126b is shown as being flush with the distal end 118c of the distal tube 118, this is for purposes of illustration only and it is understood that other configurations such as, but not limited to, angled, multifaceted or recessed configurations not extending to the distal end 118c are also within the scope of the invention.

FIG. 5a shows an another embodiment of the proximal terminal structure 226a wherein the optical fiber 16 fits in a beveled concavity 212d at the proximal end 212a of the channel 212c. It is noted that the exposed end (unnumbered) of the proximal terminal structure is concave and extends longitudinally into the proximal end 212a of the connector 212 and thus presents a greater surface area than the diameter of the optical fiber 16 would have if squarely trimmed.

FIG. 5b similarly shows an another embodiment of the distal terminal structure 226b wherein the optical fiber 16 ends at a beveled concavity 218d at the distal end 218c of the distal tube 218. It is noted that the exposed end (unnumbered) of the distal terminal structure 226b is concave and extends longitudinally into the distal end 218c of the distal tube 218 and thus presents a greater surface area than diameter of the optical fiber 16 would have if squarely trimmed. While the distal terminal structure 226b is shown as being recessed within the distal end 218c of the distal tube 218, this is for purposes of illustration only and it is understood that other configurations such as, but not limited to, configurations wherein the optical fiber 16 having a concave distal terminal structure 226b extending from the distal end 218c (not shown) are also within the scope of the invention.

It is known that the present claimed invention is able to deliver light along its length with much greater efficiency than currently existing fiber optic illumination systems, allowing an increased amount of light to be delivered from the distal end 24b, 124b, 224b of the optical fiber 16 which is collected from a lower powered light source. It is believed that the reason for this improved performance is related to the way light is propagated through the length of an optical fiber. Normally, light enters an optical fiber through an approximately square boundary angle relative to the longitudinal axis of the optical fiber. Depending on the numerical aperture of the optical fiber, only light entering the optical fiber at an angle less than the critical angle will be transmitted through the length of the optical fiber. Light at angles greater than the numerical aperture will leak out and be lost through the cladding, decreasing the relative efficiency of the optical fiber. In the present claimed invention, it is believed that the proximal terminal structure 26a, 126a, 226a functions to convert high order mode light (or at least a higher proportion of it) emitted from the light source, to low order mode light, allowing a greater amount of low order mode light energy to travel the length of the fiber optic illumination device 10. Upon the transmitted light reaching the distal terminal structure 26b, 126b, 226b it is believed that the light (or at least a higher proportion of it) is converted from low order mode light to high order mode light, resulting in a greater illumination of the target area (less light on the outer areas of the numerical aperture area) to deliver light in the target viewing area.

Method of Manufacturing

Figure 6:
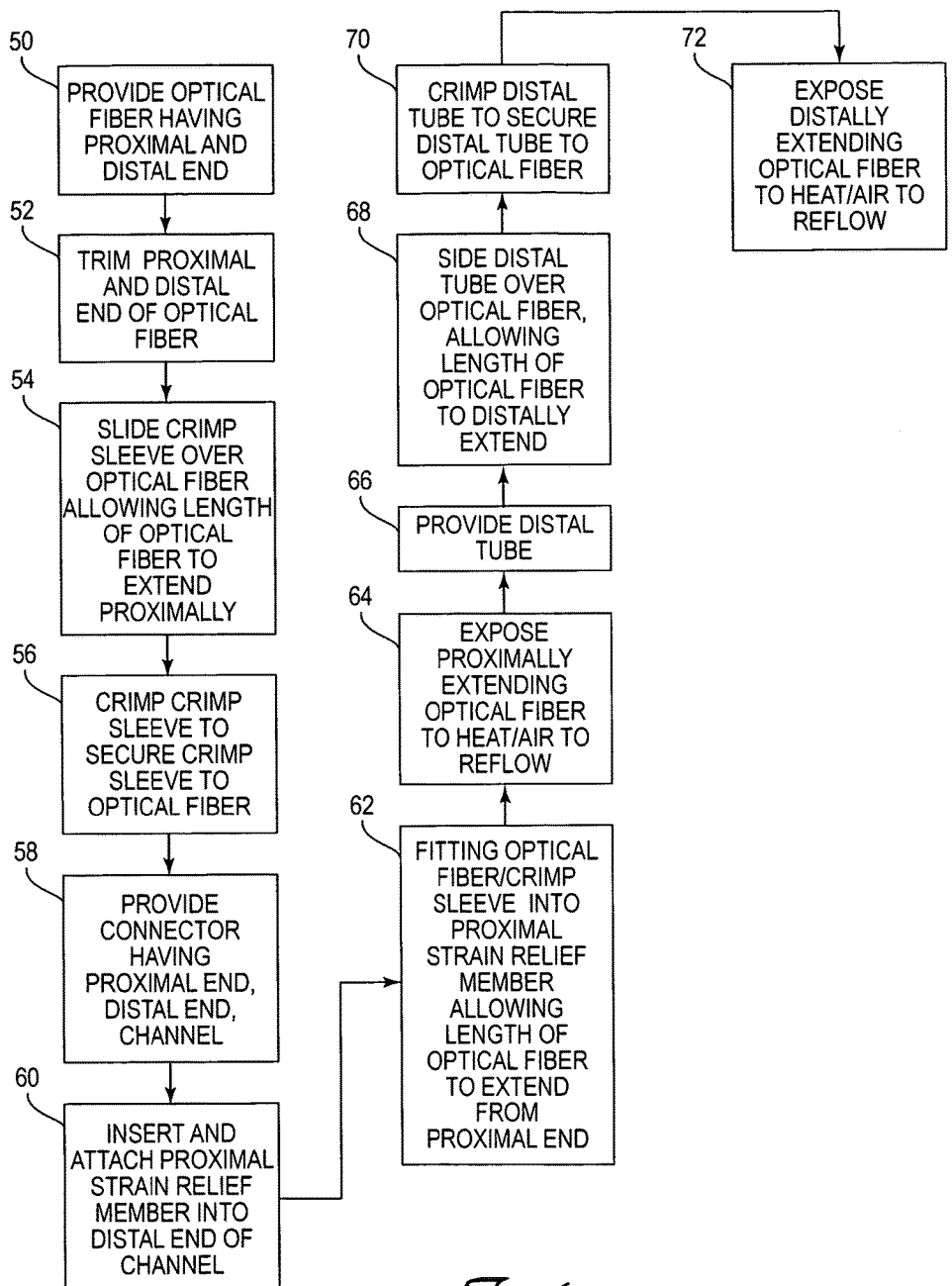
FIG. 6 is a flowchart illustrating the steps of the method of manufacturing.

FIG. 6 is a flow chart illustrating the steps involved in manufacturing the fiber optic illumination device 10 of the present invention. Preparing the proximal section 10a of the fiber optic illumination device 10 involves initially procuring 50 a length of optical fiber 16 having a proximal end 16a, a distal end 16b, an appropriate length and diameter, a cladding 20 layer and a core 24 layer. The proximal 16a and distal 16b ends of the optical fiber 16 may be trimmed 52 at this point to ensure uniformity and precision of cut. Next, a length of hypotube is slid 54 over the proximal end 16a of the optical fiber 16 allowing a portion (not shown) of the optical fiber 16 to extend from the proximal end 22a of the crimp sleeve 22 sufficient to extend through the channel 12c and from the proximal end 12a of the connector 12. The crimp sleeve 22 is exposed to a sufficient amount of external, mechanical force 56 to cause the crimp sleeve 22 to take a permanent set without damaging the optical fiber 16, thus securing the crimp sleeve 22 to the optical fiber 16.

In a separate operation a proximal strain relief member 14 is attached to the provided 58 connector 12 by inserting 60 the proximal strain relief member 14 into the channel 12c through the distal end 12b. As discussed above, the outer diameter (unnumbered) of the proximal strain relief member 14 in one embodiment is slightly larger than the outer diameter (unnumbered) of the channel 12c, resulting in an interference fit. The optical fiber 16, with attached crimp sleeve 22 is fitted 62 through the connector 12 and trimmed to extend a length of optical fiber 16 from the proximal end 12a of the connector 12. The exposed proximal end 16a of the optical fiber 16 is then exposed 64 to a sufficient amount of heat and air to cause the exposed proximal end 16a of the optical fiber 16 to reflow, resulting in the simultaneous expansion of the core 24 and cladding 20 and the formation of a proximal terminal structure 26a integral with the core 24 extending proximally from the connector 12. Due to the wide range and great variability of optical fibers available it is impossible to precisely state a sufficient amount of heat and air to cause the optical fiber to reflow. A temperature range of approximately 400-500 degrees F. at a time between approximately 2-5 seconds and airflow between approximately 5-20 standard cubic feet per minute is known to be effective in causing an optical fiber 16 to reflow, resulting in the formation of a proximal terminal structure 26a, 126a, 226a which is integral with the core 24. The formation of the proximal terminal structure 26a serves to secure the optical fiber 16 to the connector 12 without the use of chemical or mechanical fasteners and also provides a structure similar to a lens, which is integral with at least the core 24 along the length of the fiber optic illumination device 10.

In preparing the distal end 10b of the fiber optic illumination device 10 a length of hypotube is provided 66, which will function as the distal tube 18, which may be shaped to provide a specific shape required by a particular surgical retractor, surgical hardware or physician preference. Following shaping, the distal end 16b of the optical fiber 16 is slid 68 through the distal tube 18 until a sufficient length of optical fiber 16 extends distally from the distal end 18c of the distal tube 18. The distal tube 18 is exposed to a sufficient amount of external, mechanical force to cause the distal tube 18 to take a permanent set without damaging the optical fiber 16, thus crimping 70 the optical fiber 16 to distal tube 18. The distally extending end (unnumbered) of the optical fiber 16 is then attached to the distal end 18c of the distal tube 18 by means of exposing 72 the optical fiber 16 to a sufficient amount of heat and air to cause the optical fiber 16 to reflow, resulting in the simultaneous melting and expansion of the distal end 24b of the core 24 and cladding 20 and the formation of a distal terminal structure 26b integral with core 24 extending distally from the distal tube 18. Due to the wide range and great variability of optical fibers available it is impossible to precisely state a sufficient amount of heat and air to cause the optical fiber to reflow. A temperature range of approximately 400-500 degrees F. at a time between approximately 2-5 seconds and airflow between approximately 5-20 standard cubic feet per minute is known to be effective in causing an optical fiber 16 to reflow, resulting in the formation of a distal terminal structure 26b, 126b, 226b which is integral with the core 24. The formation of the distal terminal structure 26b, 126b, 226b serves to secure the optical fiber 16 from pulling through the distal tube 18 without the use of chemical or mechanical fasteners and also provides a structure similar to a lens, but which is integral with the optical fiber 16 along the length of the fiber optic illumination device 10 between the proximal terminal structure 26a to the distal terminal structure 26b, allowing uninterrupted light communication between the proximal terminal structure 26a and distal terminal structure 26b. This completes manufacture of the fiber optic illumination device 10. Sterilization and packaging area done following manufacture of the illumination device 10.

Use

Using the fiber optic illumination device 10 of the present invention involves initially preparing the patient and exposing the surgical site, following by insertion of a surgical retractor to safely maximize the area available to the surgeon during the procedure. This is followed by removing the fiber optic illumination device 10 from sterile packaging and attaching the fiber optic illumination device 10 via the proximal end 12a of the connector 12 to a light source (not shown) which could be halogen, LED or other light sources. The distal end 24b of the fiber optic illumination device 10 can then be positioned as desired by the physician and may be attached via the distal tube 18 to the retractor itself or other operating room apparatus. The light source is energized causing light to flow through the fiber optic illumination device 10, illuminating the surgical site. Following completion of the procedure, the fiber optic illumination device 10 may be disposed of.

What is claimed is:

1. An illumination device, comprising:
   an optical fiber having a proximal end, a distal end, a length, a core fiber and a cladding surrounding at least part of the core fiber;
   a connector having a proximal end and a distal end, the optical fiber extending into the connector;
   a distal tube at the distal end into which the optical fiber extends;
   wherein the proximal end of the optical fiber has a proximal terminal structure derived from the optical fiber, causing high order mode light entering the illumination device to be converted to low order mode light; and
   wherein the distal end of the optical fiber has a convex distal terminal structure derived from the core fiber and the cladding of the optical fiber extending distally out from the distal end of the distal tube and defining a wider outer diameter than the optical fiber, the distal terminal structure having a physical engagement with the distal tube and causing high order mode light to be converted into low order mode light emitted from the illumination device,
   with the proximal terminal structure, distal terminal structure and at least the core fiber being integral.

2. The illumination device of claim 1 wherein the optical fiber is a plastic optical fiber.

3. The illumination device of claim 1 wherein the optical fiber is a glass optical fiber.

4. The illumination device of claim 1 wherein the proximal terminal structure has a greater surface area than the diameter of the optical fiber.

5. An illumination device, comprising:
   an optical fiber having a proximal end, a distal end, a length, a diameter, a core fiber layer and a cladding layer surrounding at least part of the core fiber layer;
   a connector attached to the proximal end of the optical fiber having a proximal end, a distal end, and a channel extending into the connector, the channel defining a diameter;
   a crimp sleeve surrounding a portion of the optical fiber and crimpingly secured over the outer dimension of the optical fiber;
   a proximal strain relief member surrounding a portion of the crimp sleeve, the proximal strain relief member secured to the outer diameter of the channel extending through the connector;
   a distal tube attached to the distal end of the optical fiber defining a distal end and configured to receive the optical fiber;
   wherein the proximal end of the optical fiber has a proximal terminal structure derived from the optical fiber having a greater surface area than the diameter of the optical fiber and causing high order mode light entering the illumination device to be converted to low order mode light, and
   wherein the distal end of the optical fiber has a convex distal terminal structure derived from the core fiber layer and the cladding layer of the optical fiber extending distally out from and providing physical engagement with the distal end of the distal tube and defining a wider outer diameter than the optical fiber and causing high order mode light to be converted into low order mode light emitted from the illumination device, with the proximal terminal structure, the distal terminal structure and the core fiber being integral.

6. The illumination device of claim 5 wherein the optical fiber is a plastic optical fiber.

7. The illumination device of claim 5 wherein the optical fiber is a glass optical fiber.

8. A method of manufacturing a fiber optic illumination device, comprising the steps of:
   a) preparing a proximal section of the illumination device by:
      i) providing an optical fiber having a proximal end, a distal end, an outer diameter, a length, a cladding layer and a core layer;
      ii) trimming the proximal end and the distal end of the optical fiber;
      iii) sliding a length of crimp sleeve over the proximal end of the optical fiber, allowing a length of optical fiber to extend from the crimp sleeve;
      iv) crimping the crimp sleeve with sufficient mechanical force to cause the crimp sleeve to take a permanent set to secure the crimp sleeve to the optical fiber without damaging the optical fiber;
      v) providing a connector having a proximal end, a distal end and a channel extending there through;
      vi) inserting and attaching a proximal strain relief member into the distal end of the channel in a manner allowing a portion of the proximal strain relief member to extend distally from the connector;
      vii) fitting the optical fiber with attached crimp sleeve into the connector through the proximal strain relief member to allow a length of optical fiber to extend from the proximal end of the connector;
      viii) exposing the end of the optical fiber extending from the proximal end of the connector to a sufficient amount of heated air to cause the core layer and the cladding layer of the proximal end of the optical fiber to reflow, creating a first structure extending from the proximal end of the connector having a diameter wider than the optical fiber prior to reflowing; and
   b) preparing a distal end of the illumination device by:
      i) providing a distal tube;
      ii) sliding the distal tube over the optical fiber allowing a length of optical fiber to extend from a distal end of the distal tube, the length of optical fiber extending from the distal end of the distal tube containing core layer and cladding layer;
      iii) crimping the distal tube with sufficient mechanical force to cause the distal tube to take a permanent set to secure the distal tube to the optical fiber without damaging the optical fiber; and
      iv) exposing the end of the optical fiber extending from the distal end of the distal tube with a sufficient amount of heated air to cause the core layer and the cladding layer of the distal end of the optical fiber to reflow, creating a convex, second structure extending from the distal end of the distal tube having a diameter wider than the optical fiber prior to reflowing, resulting in a fiber optic illumination device with an integral light communication path between the proximal end of the illumination device and the distal end of the illumination device.

9. The method of claim 8 wherein the optical fiber is a plastic optical fiber.

10. The method of claim 8 wherein the optical fiber is a glass optical fiber.

11. A method of manufacturing a fiber optic illumination device, comprising the steps of:
    a) preparing a proximal section of the illumination device by:
       i) providing an optical fiber having a proximal end, a distal end, an outer diameter, a length, a cladding layer and a core layer;
       ii) sliding a length of crimp sleeve over the proximal end of the optical fiber, allowing a length of optical fiber to extend from the proximal end of the crimp sleeve;
       iii) crimping the crimp sleeve with sufficient mechanical force to cause the crimp sleeve to take a permanent set to secure the crimp sleeve to the optical fiber without damaging the optical fiber;
       iv) providing a connector having a proximal end, a distal end and a channel extending there through;
       v) inserting and attaching a proximal strain relief member into the distal end of the channel in a manner allowing a portion of the proximal strain relief member to extend distally from the connector;
       vi) fitting the optical fiber with attached crimp sleeve into the connector through the proximal strain relief member to allow a length of optical fiber to extend from the proximal end of the connector;
       vii) exposing the end of the optical fiber extending from the proximal end of the connector to a sufficient amount of air and heat to cause the proximal end of the optical fiber to reflow, creating a first structure extending from the proximal end of the connector having a diameter wider than the optical fiber prior to reflowing; and
    b) preparing a distal end of the illumination device by:
       i) providing a distal tube;

ii) sliding the distal tube over the optical fiber allowing a length of optical fiber to extend from a distal end of the distal tube, the length of optical fiber extending from the distal end of the distal tube containing core layer and cladding layer;
iii) crimping the distal tube with sufficient mechanical force to cause the distal tube to take a permanent set to secure the distal tube to the optical fiber without damaging the optical fiber; and
iv) exposing the end of the optical fiber extending from the distal end of the distal tube with a sufficient amount of air and heat to cause the distal end of the optical fiber to reflow, creating a convex second structure extending from the distal end of the distal tube having a diameter wider than the optical fiber prior to reflowing, resulting in a fiber optic illumination device with an integral light communication path between the proximal end of the illumination device and the distal end of the illumination device;

wherein the proximal end of the optical fiber and the distal end of the optical fiber are exposed to heated air at a temperature of approximately between 400-500 degrees F. at a time between approximately 2-5 seconds at an airflow of approximately 5-20 standard cubic feet per minute.

\* \* \* \* \*